United States Patent [19]

Brossi et al.

[11] Patent Number: 5,039,801

[45] Date of Patent: Aug. 13, 1991

[54] THERMAL FRAGMENTATION OF METHYLBENZYLUREA DISASTEREOMERS OR SECONDARY AMINES AND PREPARATION OF OPTICALLY ACTIVE SECONDARY AMINES

[75] Inventors: Arnold Brossi; Bernhard Schonenberger, both of Bethesda, Md.

[73] Assignee: The United States of America as represented by the Department of Health & Human Services, Washington, D.C.

[21] Appl. No.: 90,363

[22] Filed: Aug. 28, 1987

Related U.S. Application Data

[63] Continuation-in-part of Ser. No. 811,425, Dec. 20, 1985, abandoned.

[51] Int. Cl.[5] .................. C07D 471/04; C07C 209/88
[52] U.S. Cl. ..................................... 546/85; 546/146; 560/24; 560/338; 560/344; 560/345; 564/56; 564/302; 564/303; 564/304; 564/414
[58] Field of Search ................. 564/56, 302, 303, 304, 564/414; 546/85, 146; 560/24, 338, 344, 345

[56] References Cited

U.S. PATENT DOCUMENTS

| 1,792,156 | 2/1931 | Fitzky | 564/414 X |
|---|---|---|---|
| 2,046,375 | 7/1936 | Goldstein et al. | 564/414 X |
| 2,056,255 | 10/1936 | Coffey et al. | 564/414 X |
| 2,810,754 | 10/1957 | Chang et al. | 564/56 X |
| 3,168,566 | 2/1965 | Loter et al. | 564/302 |
| 3,404,103 | 10/1968 | Matsudaira et al. | 564/414 X |
| 3,405,159 | 10/1968 | Krieger et al. | 564/304 X |
| 3,682,925 | 8/1972 | Hollander et al. | 564/304 X |
| 3,755,413 | 8/1973 | Koppe et al. | 564/56 X |
| 3,857,889 | 12/1974 | Leigh | 564/304 |
| 4,463,176 | 7/1984 | Dennis et al. | 564/303 X |

OTHER PUBLICATIONS

Fieser et al., "Reagents for Organic Synthesis", vol. 8*, p. 499 (1980).
Fieser et al., "Reagents for Organic Synthesis", vol. 11, pp. 553–554 (1984).

Primary Examiner—Richard L. Raymond
Attorney, Agent, or Firm—Robert Benson

[57] ABSTRACT

The invention provides an improved method for obtaining optically active amines, carbamates, and isocyanates by thermal fragmentation of optically active ureas through refluxing the ureas in $C_3$–$C_7$ alcohol solution with or without catalytic amounts of alkali metal.

16 Claims, No Drawings

THERMAL FRAGMENTATION OF METHYLBENZYLUREA DISASTEREOMERS OR SECONDARY AMINES AND PREPARATION OF OPTICALLY ACTIVE SECONDARY AMINES

This application is a continuation-in-part of U.S. Ser. No. 06/811,425, filed Dec. 20, 1985, now abandoned.

BACKGROUND OF THE INVENTION

Chemical resolution of chiral (±)-secondary amines with optically active acids is the classical method to prepare the optical antipodes of these amines. Many examples are cited in the text by Paul Newman "Optical Resolution for Chemical Compounds: Vol. 1: Amines and Related Compounds", Opt. Resolution Inf. Center, Manhattan College, Riverdale, N.Y. 10471 (1976). Chemical resolution is used in the total synthesis of (−)-emetine, (−)-salsolidine, and (+)-N-norreticuline required for a total synthesis of opium alkaloids. Chemical resolution is a critical step in the synthesis of optically active amines which, if used as drugs, have to be optically pure. Analytical methods to measure optical purity were developed by reacting optically active secondary amines with commercially available R-(+)- or S-(−)-methylbenzylisocyanate, or naphthylethyl analogs, and were frequently used. In this reaction, illustrated in Scheme 2 optically active methylbenzylureas (−)-B and (−)-C are formed which can be separated by chromatographic methods, such as HPLC, TLC, or column chromatography on silica gel or aluminum oxide, or simply by crystallization from solvents, water, or solvent mixtures. The composition of the reaction mixture can be analyzed by $^1$H-NMR techniques, and optical purity, or the degree of optical impurity be calculated. This in principle elegant method for separating secondary amines in form of methylbenzylurea derivatives, is lacking synthetic utility, since these ureas could not be converted into optically active amines.

Secondary amines biologically active as one of the two optical isomers are represented by (−)-emetine (Merck Index 3523), a useful amebicide, and (+)-mecamylamine, a useful antihypertensive drug as the racemate (Merck Index No. 5595). A separation of racemic normorphinans into optical isomers affords the (−)-enantiomer which can be converted into the narcotic analgetic drug dromoran (Merck Index No. 5297), and the (+)-isomer which can be converted into the antitussive agent dextromethorphan (Merck Index No. 8009), and is described by Hellerbach et al. in "Synthetic Analgesics, Part II (A) Morphinans." Secondary amines can be converted into primary amines or tertiary amines by well established chemical reactions shown below. A successful resolution of secondary amines, therefore, in principle also includes the preparation of optically active primary and tertiary amines.

Such methods include formation of a Schiff base from a primary amine I with an aldehyde and reduction to the secondary amine by borohydrides or catalytically. The Nbenzyl substituted secondary amine II is a secondary amine which, can after successful resolution, be reconverted into the primary amine I by catalytic debenzylation, or further alkylated to a tertiary amine III, also obtainable from I by direct alkylation, or from II by reaction with chloroformates and reduction of the carbamate with LAH.

A practical method for resolving enantiomeric mixtures of secondary amines, therefore, provides an entry into optically active primary amines exemplified with (+)-amphetamine called dextroamphetamine (Merck Index No. 2918), an appetite suppressant, or tertiary amines such as (−)-physostigmine (Merck Index No. 7267), an anticholinesterase agent useful in treating Alzheimers disease.

Scheme 1

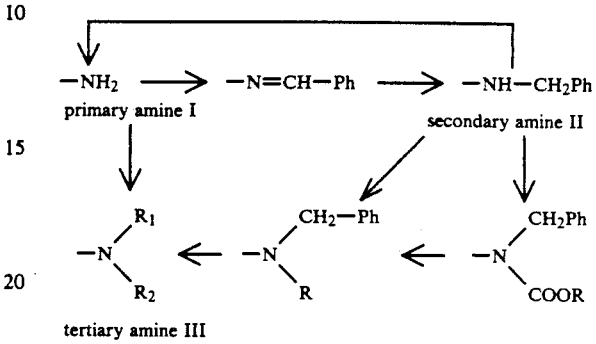

SPECIFIC METHOD OF THE INVENTION

It has now been found that preparation of optical isomers can be achieved by heating pure α-methylbenzyl- or 1-naphthylethylurea diastereomers of secondary amines, in refluxing alcohols, having 2–7 carbon atoms with or without addition of alkali metal. The α-methylbenzyl- or 1-naphthylethyl part of the ureas can be aromatically substituted. By this reaction, which is illustrated below, optically active secondary amines of high optical purity are directly obtained. Neutral methylbenzylcarbamates, or naphthylethyl carbamates originating from the methylbenzylamine or (1-naphthyl)ethylamine can be used as examples. The optically active amines can be isolated as materials soluble in aqueous acids, such as hydrochloric acid, sulfuric acid etc., or converted into crystalline salts with oxalic acid, fumaric acid, hydrobromic acid etc., in an appropriate solvent such as acetone, alcohol, ethylacetate etc. The methylbenzyl- or naphthylethyl-carbamates can be reconverted into optically active isocyanates with trichlorosilane, or by hydrolyzing the esters with base, affording optically active methylbenzylamine or naphthylethylamine, respectively, which upon reaction with phosgene affords directly the original optically active isocyanates.

Particularly preferred alcohols are those having boiling temperatures of 78° C. to 200° C. Most preferred are those having boiling temperatures of 90° C. to 200° C.

ADVANTAGES OF THE INVENTION

The advantage of this method of resolution lies in the fact that separation of both methylbenzylureas or their analogs, can often be achieved in high yield, and they can quantitatively be converted into optically pure amines and carbamates in one simple step, thus allowing not only preparation of both optical antipodes of secondary amines in equal yield, but also allowing at the same time recovery of carbamates useful for conversion into the original isocyanates.

This invention provides that thermal decomposition of methylbenzyl- or naphthylethylurea derivatives of secondary amines containing chirality and obtained as optically pure entities, can be converted by thermal decomposition in refluxing alcohols, in the presence or without alkali metals, into optically active secondary amines of high optical purity and optically active methylbenzyl- resp. naphthylethylcarbamates, reconvertible into optically active isocyanates.

Scheme 2

This is illustrated in Scheme 2: The secondary amine (±)-A having a chiral carbon substituted with $R_1$ and $R_2$, when reacted with S-(−)-methylbenzylisocyanate affords the methylbenzyl urea diastereomers (−)-B and (−)-C which were separated, besides the neutral carbamate (−)-D. The latter was converted into the amine (−)-E by alkaline hydrolysis, and this into the isocyanate (−)-F by reaction with phosgene. Both urea diastereomers (−)-2 and (−)-3, when refluxed in alcohol such as butanol or amylalcohol, quickly in the presence of sodium, and slowly without sodium afford optically active secondary amines (+)-1 and (−)-1 in high yield, isolated i.e. by extraction with aqueous acid, basification with NaOH or $NH_4OH$ and extraction with a solvent such as dichloromethane, toluene, ether etc. The free bases obtained were converted into crystalline salts such as hydrochlorides, sulfates, fumarates, succinates by conventional methods.

The invention is described with several examples of biologically interesting secondary amines, already resolved by classical chemical resolution to show the usefulness and advantages of the new method: (±)-mecamylamine, a well known antihypertensive agent, was resolved by classical resolution which turned out to be tedious, affording the desired optical antipodes only in low yield. In contrast, the optical antipodes (−)- and (+)-mecamylamine were obtained here from the corresponding methylbenzylureas in 40% yield each and were of high optical purity (95%, HPLC), affording hydrochloride salts which were optically pure after one crystallization. The indole alkaloid (±)-N1-noreseroline-O-methyl ether, an important intermediate in the synthesis of (−)- and (+)-physostigmine when used as its O-ethylether derivative eserethole, could only be resolved with tartaric acid in low yield requiring several recrystallizations to achieve purification. Thermal decomposition of methylbenzylurea diastereomers separated by column chromatography in refluxing n-amyl alcohol, and in the presence of 1 equ. Na, afforded (−)- and (+)-N1-norseroline-O-methyl ether (optical purity 95%, HPLC) in 37% yield, besides the n-amylcarbamate of methylbenzylamine. The latter could be converted into methylbenzylamine and R-(+)-methylbenzylisocyanate. Classical chemical resolution of the isoquinoline alkaloids (±)salsolidine, readily available from dehydrosalsolidine, by reduction, was accomplished with tartaric acid. By the new method described here both (−)- and (+)-salsolidine were obtained in 33% yield each, and found optically pure after one crystallization of the hydrochlorides (98%, HPLC). The indole alkaloid tetrahydroharmine found in Pegala harmala is a natural product. The new method described here afforded (−)- and (+)-tetrahydroharmine of good optical purity after HPLC-separation of methylbenzylureas, thermolysis in butanol and crystallization of their tartrates. Primary amines can readily be converted into secondary amines by N-alkylation. When N-benzyl or substituted N-benzyl is introduced, best by formation of a Schiff base from the amine and an aldehyde as shown in the case of (±)-amphetamine, reduction with borohydride affords substituted N-benzyl-substituted secondary amines, which can be resolved with the present method illustrated with opt. active 1-naphthylethylisocyanates as reagents which are commercially available. Reductive N-debenzylaton of (−)- and (+)- N-vanillylamphetamines in acetic acid over Pd-catalyst, afforded optically pure (−)and (+)-amphetamine respectively with optical purity greater than 99% (HPLC).

Abbreviations: methylbenzyl = α-methylbenzyl
naphthylethyl = 1-(1-naphthyl)-ethyl Scheme 2: Illustrated by the foregoing.

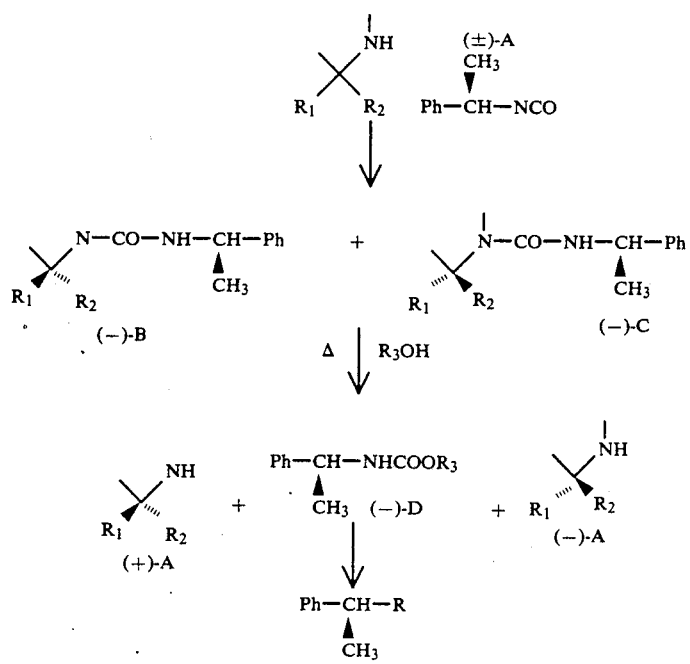

Scheme 2: Illustrated by the foregoing.

(−)-E  R = NH$_2$
(−)-F  R = NCO

EXAMPLE 1

(1S)-11-(N-(S)-methylbenzyl-carbamoyl-mecamylamine (2) and its (1R)-analog 3

A solution of 3.19 g (15.66 mmol) (±)mecamylamine hydrochloride ((±)-1.HCl) in 40 ml half-saturated, aqueous Na$_2$CO$_3$ was extracted with ether (3×30 ml), the organic phase dried over MgSO$_4$ and concentrated in vacuo. The residue was uptaken in 30 ml CHCl$_3$ and mixed at room temperature with 2.30 g (15.65 mmol) S-(−)- α-methylbenzylisocyanate. The solution was stirred for 1 h, then concentrated in vacuo and the residue chromatographed on a silica gel-column with ether/hexane=1/5, which gave 2.11 g (43%) less polar fraction (oil that crystallized slowly on standing) and 2.62 (53%) more polar and mixing fraction (oil that crystallized rapidly on standing). The less polar fraction was recrystallized from hexane to give 1.65 g 2 as colorless needles: mp 91.5-9220 -[α]D=−71.8° (c=0.7 in CHCl$_3$); The more polar fraction was recrystallized from diisopropylether to give 1.85 g 3 as colorless crystals: mp 108°-108.5°; [α]$_D$=+44.1° (c=0.9 in CHCl$_3$).

(S)-(−)α-Methyl-benzylamin((−)-13))

A solution of 640 mg (3.31 mmol) carbamate (−)-12 in 10 ml H$_2$O/EtOH/KOH=10:40:5 was refluxed for 44 hrs, the acidified with 2[M]HCl and concentrated to remove the EtOH. The resulting suspension was basified with 10% NaOH, extracted with Et$_2$O (4×10 ml) and the dried (MgSO$_4$) extract concentrated to a volume of about 10 ml. Addition of 1 equivalent of HCl in MeOH gave 271 mg (52%) hydrochloride (−)-13.HCl: mp. 169°-17120 , lit.[20] 171°. From this hydrochloride the base was freed and distill (Kugelrohr, 15 torr, 120°): [α] −38.4° (c=1.9 in CHCl$_3$); a reference sample (Aldrich) had [α]$_D$ −34.7° (c=2.1 in CHCl$_3$).

(+)-Mecamylamine-hydrochloride ((+)-1.HCl) and its enantiomer (−)-1.HCl

A solution of 2.46 g (7.82 mmol) urea 2 in 10 ml abs. EtOH was slowly mixed with 20 ml 2[M] NaOEt in EtOH at r.t., then refluxed for 45 min. The r.m. was cooled to r.t., concentrated in vacuo by using a Vigreux-column, the residue acidified with enough 2[M]HCl, extracted with Et$_2$O (2×20 ml). The etheral extract of the concentrated, acidified reaction mixture was concentrated and the residue distilled (Kugelrohr, 180°, 20 torr) to give 6.08 (96%) (−)-12 as a tlc. pure, colorless liquid which turned to a waxy solid on standing in cold: [α]$_D$=−77.0° (c=2.6 in benzene) lit. (+)-12: ,[α]$_D$=+80.1° (c=3 in benzene). The combined org extracts from the alkaline aqueous phase were concentrated, the resulting liquid was mixed with 20 ml Et$_2$O and crude hydrochloride (+)-1.HCl was precipitated by addition of a slight excess of HCl in Et$_2$O. After filtration the finely powdered colorless solid was recrystallized from 2-propanol to give 1.02 g (64%) (+)-1.HCl as needles [α]$_D$+20.1° (c=1.7 in CHCl$_3$). The more polar urea 3 (1.85 g, 5.89 mmol) was treated in exactly the same manner to give 752 mg (63%) (−)-1.HCl as colorless needles: [α]$_D$−20.0° (c=2.2 in CHCl$_3$).

Resolution of mecamylamine as described in Example 1 is shown below.

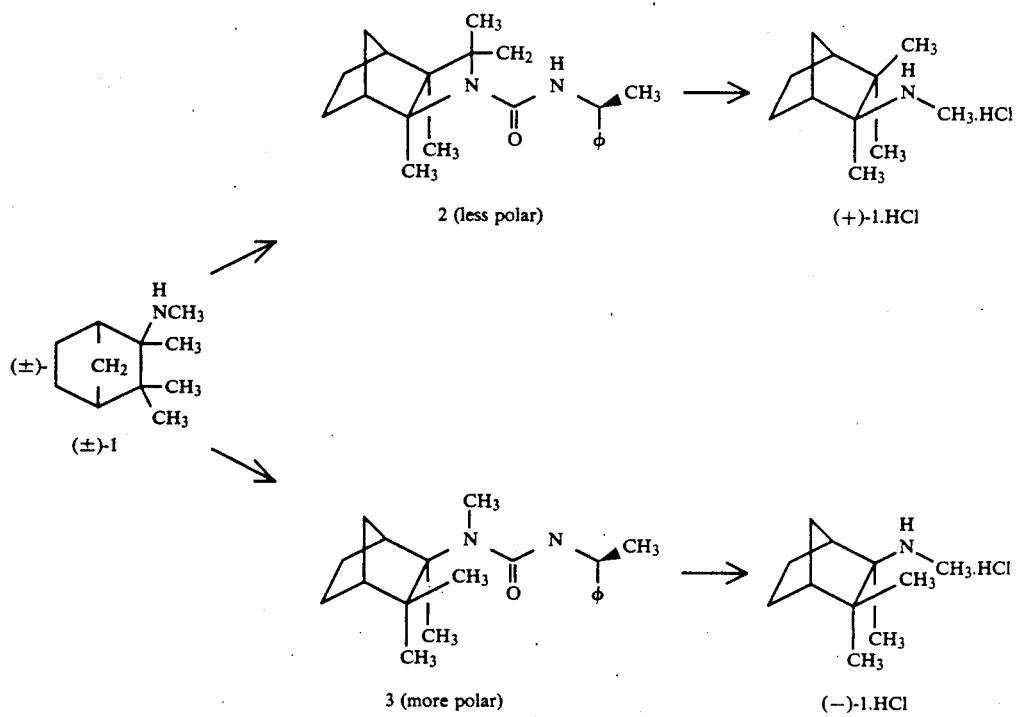

-continued
Resolution of mecamylamine as described in Example 1 is shown below.

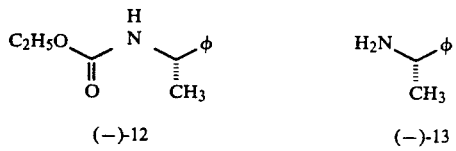

(−)-12    (−)-13

EXAMPLE 2

A solution of 152 mg (0.48 mmol) of the less polar urea 2 in 2 ml n-propanol was refluxed, until tlc. showed absense of starting material (4 h). The reaction mixture was mixed with 2 ml of 2[M]HCl, extracted with 5 ml Et₂O, basified with enough 10% NaOH and extracted with Et₂O (3×5 ml). These etheral extracts were concentrated to about 5 ml and enough HCl in Et₂O added to precipitate all (+)-mecamylaminehydrochloride ((+)-1.HCl) (56 mg (57%) after recrystallization as described in example 1).

(10R)-1-Nor-1-(N-(S)-αmethyl-benzyl)-carbamoyl-eserolinemethylether (5) (less polar).

Oil that crystallized slowly on standing: mp 124°–125° C. (from CH$_2$Cl$_2$/diisopropylether); [α]D+182.9° (c=0.9 in CHCl$_3$);

(10S)-1-Nor-1-(N-(S)-αmethylbenz-yl)-carbamoyl-eserolinemethyl- ether (6) (more polar)

Foam; [α]$_D$+40.0° (c=1.7 in CHCl$_3$);

Example 3 is further illustrated below.

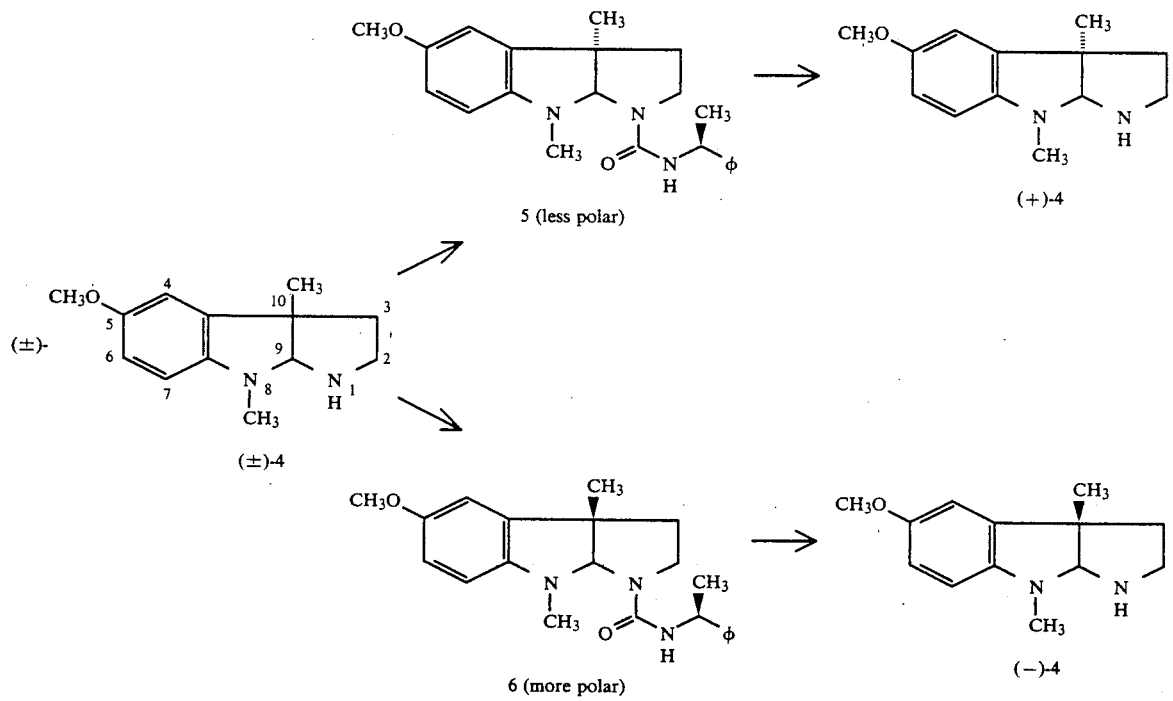

EXAMPLE 3

Synthesis and separation of the diastereomeric ureas 5 and 6

To a stirred, cold solution (0° C.) of 1.20 g (5.49 mmol) (±)1-Noreserolinemethylether ( (±)-4) in 12 ml CHCl$_3$ 889 mg (6.04 mmol) S-(−) -α-methylbenzylisocyanate was dropwise added. After 2 h the reaction mixture was concentrated in vacuo and the residue chromatographed on a silica gel column with CH$_2$Cl$_2$:MeOH=100:1 to 80:1) which gave 736 mg (37%) of the less polar urea 5, 803 mg (40%) of the more polar urea 6 and 441 mg (22%) mixing fraction. The diastereomeric purity of 5 and 6 was 95% according to HPLC.

EXAMPLE 4

(10R)-(+)-1-Noreserolinemethylether ((+)-4)

A solution of 4.53 g (12.39 mmol) urea 5 in 45 ml 1[M] nPentONa in n-PentOH was refluxed for 1 h, then cooled and rendered acidic by dropwise addition of 6 ml conc. HCl. The reaction mixture was concentrated at high vacuum, the residue uptaken in 50 ml 0.5 [M@ HCl and extracted once with 50 ml Et$_2$O. The aqueous phase was basified with aqueous, saturated Na2CO3, extracted with CHCl$_3$ (3×50 ml), the combined org. phase dried (MgSO$_4$), concentrated and the residue. chromatographed on silica gel (CH$_2$Cl$_2$:MeOH=15 l), which gave 2.51 g (93%) (+)-4 as an oil: [α]D= +35.2$_0$ (c=1.8 in CHCl$_3$); IR, H-NMR and MS are identical with those of the racemic material (+)-4. An oxalate was precipitated by addition of 1 equivalent oxalic acid (1[M] in EtOH) to a solution of (+)-4 in EtOAc. Recrystallization from EtOH/diisopropylether yielded fine, colorless crystals: mp 151°-153° [α]D+68.0° (c=0.8 in MeOH).

(1R)-2-(N-(R)-α-methylbenzyl-carbamoylsalsolidine (9)

The combined mother liquors from 8 were concentrated in vacuo, the residue chromatographed on silica gel (AcOEt:

Example 6 is illustrated below:

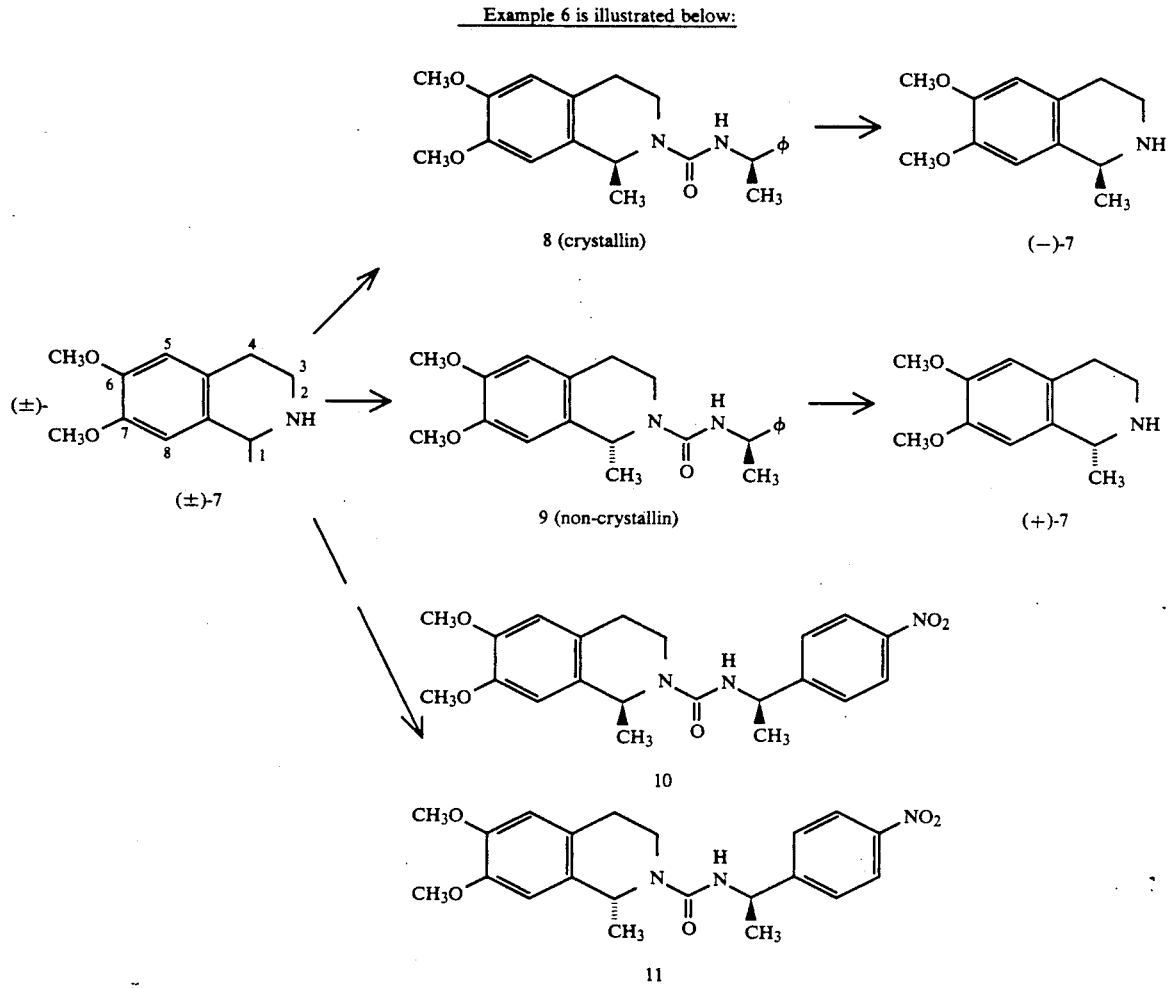

EXAMPLE 5

(10S)-(−)-1-Noreserolinemethylether ((−)-4)

Urea 6 was treated in exactly the same way as 5 to give (−)-4 as oil an oil: [α]D −38° (c=3.0 in CHCl₃) Oxalate: mp. 156°-153°; [α]_D−77.2° (c=0.7 in MeOH).

EXAMPLE 6

(1S)-2-(N-(R)α-methylbenzyl)-carbamoylsalsolidine (8)

To a stirred, cold solution (0° C.) of 2.07 g (9.99 mmol) (±)-salsolidine ( (+)-7) in 20 ml CHCl₃ 16 g (10.87 mmol) R-(+)α-methylbenzylisocyanate was dropwise added. After 1 h the reaction mixture was concentrated in vacuo, the residue solved in 2 ml CH₂Cl₂ and 10 ml diisopropylether added to this solution, which was, after addition of a seed crystal of 8, kept in the refrigerator overnight. Filtration and recrystallization of the colorless crystals from CH₂Cl₂/diisopropyl ether gave 1.61 g (46%) of 8 which was free of its diasteromers 9 according to HPLC mp 199°-202°; [α]_D+48.0° (c=0.7 in CHCl₃);

hexane=1:1) and from the resulting oil a second crop of 8 (133 mg) was crystallized, which was strongly contaminated with 9 according to HPLC. The remaining mother liquor contained 1.61 g (44%) almost pure, non-crystallin urea 9 with only traces of 8: [α]_D−101.5 (c=0.9 in CHCl₃)

(1S)-(−)-Salsolidine-hydrochloride ((−)-7.HCl)

A suspension of 1.58 g (4.46 mmol) urea 8 in 10 ml 2 [M] n-But ONa in n-ButOH was heated to boiling temp. and the resulting solution refluxed for 2 h. The reaction mixture was then cooled to room temp., 15 ml 2 [M] HCl was added and the acidic solution concentrated on high vacuum to about 10 ml. The resulting 2-phase system was, after addition of a few drops of conc. HCl, kept overnight in the refrigerator which gave after filtration a first crop of hydrochloride (−)-7. HCl. Extraction of the acidic aqueous phase with 10 ml Et₂O, rendering basic by addition of enough 10% NaOH, again extraction of the aqueous solution with CH₂Cl₂ (3×10 ml) and dissolution of the CH₂Cl₂-extract in 10 ml 2[M] HCl gave, after addition of a seed crystal a second crop of (−)-7.HCl. Total yield: 810 mg (74%). Recrystallization from 2[M] HCl gave colorless crystals: mp. 238°-240°; [α]_D−25.6° (c=2.1 in H₂20) .

(1R)-(+)-Salsolidine-hydrochloride ((+)-7.HCl).

The non-crystallin urea 9 was treated in exactly the same way as 8 to give (+)-7.HCl: mp 240°-242°, $[\alpha]_D +24.1°$ (c=1.8 in H₂O).

EXAMPLE 7

(1S)-2-(N-(R)-1-p-Nitrophenyl)-ethyl)-carbamoylsalsolidine (10) and its (1R)-diasteromer 11

A solution of 392 mg (2.36 mmol) (R)-1-(p-Nitrophenyl)-ethyl-amine in 5 ml CHCl₃ was dropwise mixed with 2.2 nl COCl₂-solution (12.5% in toluene) at 0. The resulting suspension was stirred at r.t. for 2 h, then refluxed for 1 h and then concentrated in vacuo to dryness 5 ml CHCl₃ was added and then at r.t. a solution of 476 mg (2.36 mmol) (±)-salsolidine ((±)-7) in 2 ml CHCl₃. After 15 min. the resulting clear solution was mixed with 5 ml H₂O, the phases separated and the aqueous phase extracted with CHCl₃ (2×5 ml). The residue was chromatographed on a silica gel column (30 mm diam., 20 cm length, Example 8 is illustrated below:

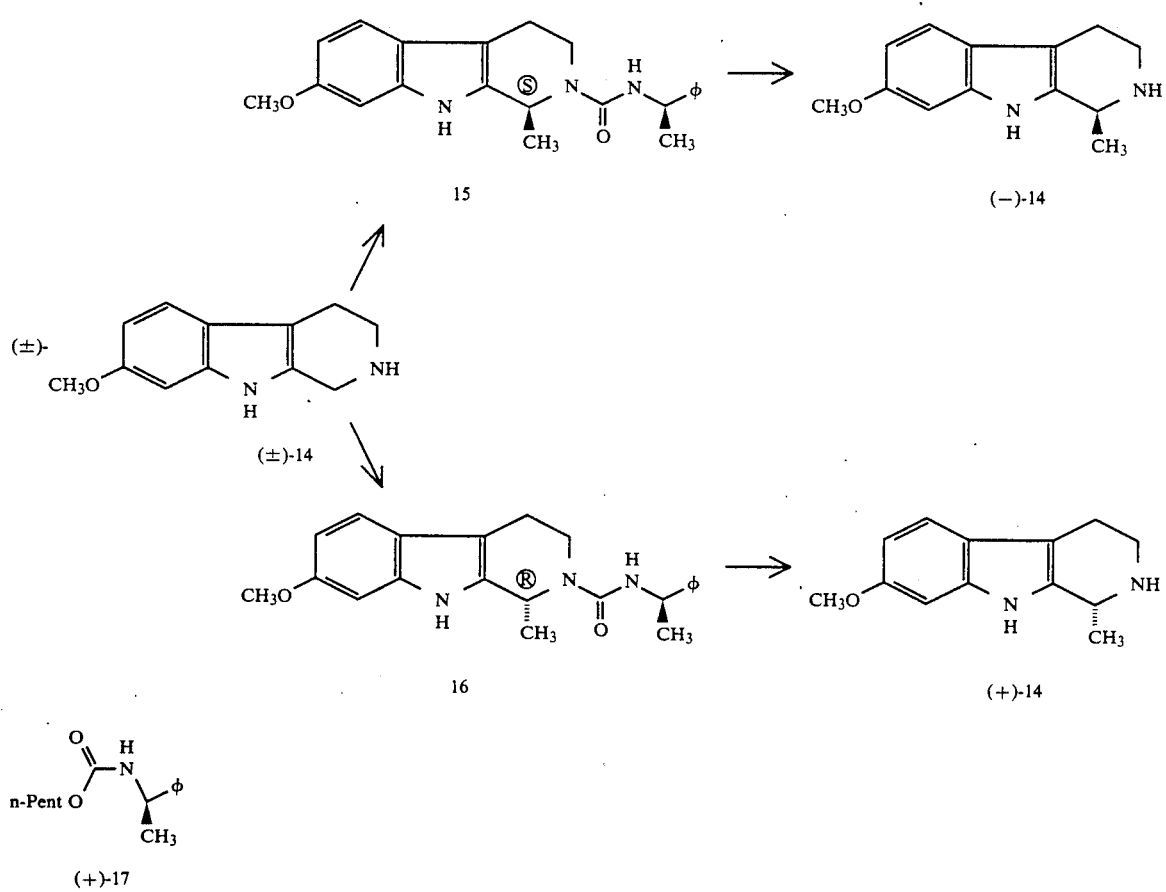

Example 9 is illustrated below:

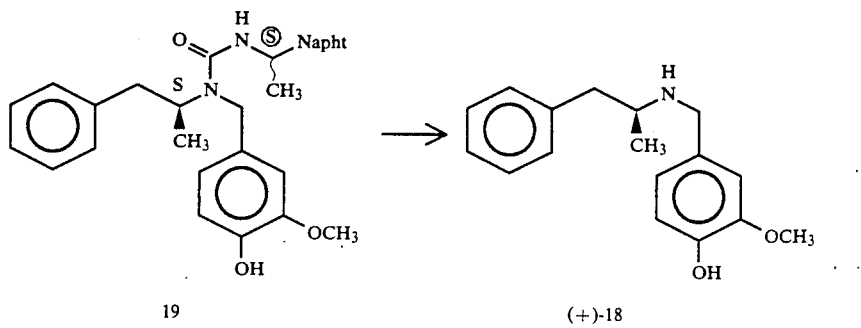

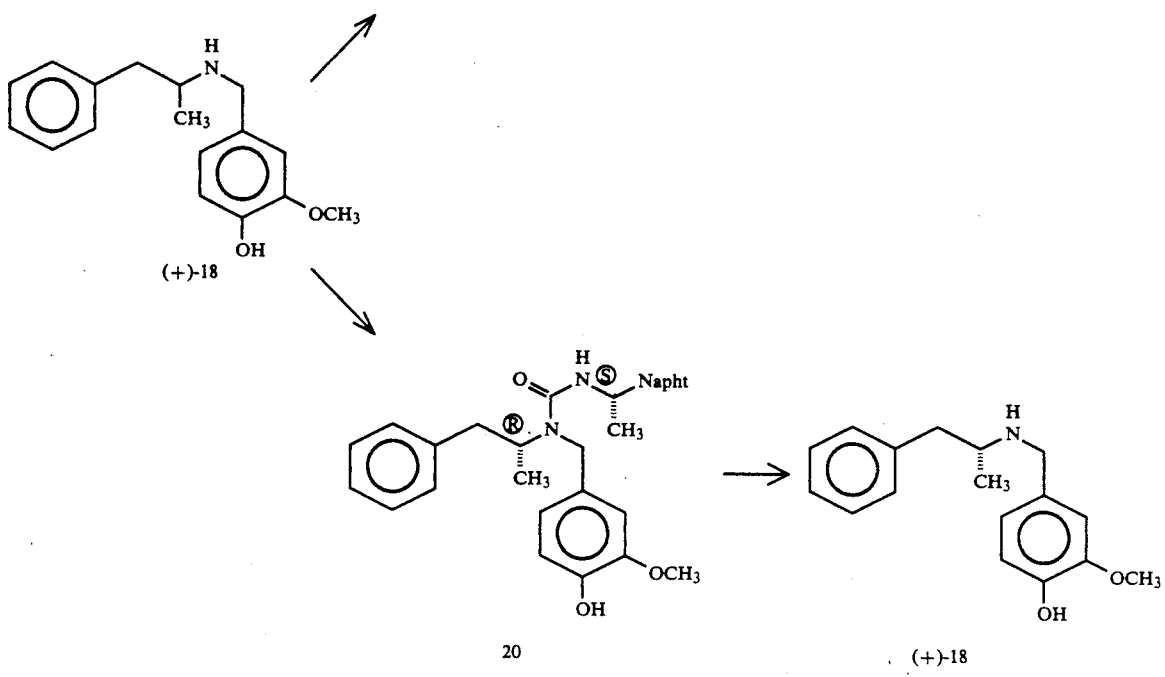

3 lbs pressure, AcOEt: hexan=2:1) to give 230 mg of a 1:1 mixture of 10 and 11 as a slowly crystallizing oil which can be separated into the diasteromers by analytical HPLC: MS (EI) 400 (M++1).

EXAMPLE 8

(1S)-2-(N-(R)αmethylbenzyl)-carbamoyl-tetrahydroharmine (15) and its (1R)-diasteromer 16

A suspension of 2.93 g (13.54 mmol) amine (±)-14 in 20 ml CHCl₃ was dropwise mixed with 2.19 g (14.90 mmol) R-(+)- -methyl-benzylisocyanate. After 1 h the resulting solution was shaken with 100 ml 0.1 [M] H₂S₄ and extracted with CHCl₃ (4×50 ml) which gave, after concentration, a solid residue. Preparative HPLC separation (silica gel, AcOEt:hexane=1:3) gave 1.26 (26%) less polar diasteromers 15 with a diasteromeric purity of 75% (anal. HPLC). Repurification of an analytical sample with semi-preparative HPLC gave pure, crystallin 15: mp. 111°-114° (from CH₂Cl₂/Et₂O); $[α]_D$—158.5° (c=0.6 in CHCl₃); IR (CHCl₃) 3460, 3280, 2910, 2830, 1620, 1144; MS (EI) 364 (M+1,40), 217(100), 213(50).

Besides a mixing fraction of 0.83 g (17%) the more polar diasteromers 16 was received as a solid, which was recrystallized from CH₂Cl₂/Et₂O to give 1.53 g (31%) with a diasteromer purity of 75% (anal. HPLC). Further recrystallization did not improve this ratio. (1R)-(+)-Tetrahydroharmine ((+)-I4). A solution of 0.79 g (2.17 mmol) urea 16 (contaminated with 25% 15) in 10 ml 1 [M] n-PentONa in n-PentOH was refluxed for ½ hr., then acidified with 2[M]HCl, extracted with Et2O (1×10 ml), basified with 10% NaOH and extracted with CHCl3 (3×10 ml). The CHCl3 extract was concentrated and the solid residue recrystallized from EtOH to give 208 mg (55%) (+)-14 with an optical purity of 74% according to $[α]_D$—19.6° C., (CHCl₃)

The etheral extract of the acidified reaction mixture was conc. on high vacuum to about 5 ml, a part of it chromatographed on a silica gel column (20 mm diam., 20 cm length, 1 lbs pressure, Et₂O: hexane=1.2) and the desired fraction distilled (Kugelrohr, 230°, 1 torr) to give carobamate (+)-17 as a colorless oil: $[α]D+52$ 8° (c=4.4 in CHCl₃); MS (EI) 236 (M++1, 95), 153 (100).

EXAMPLE 9

N-(N'-(S)-1-naphthyl-ethyl)-carbamoyl-N-vanillyl-(S)-amphetamine 19 and its (R)-amphetamine-diasteromer 20

To a solution of 1.84 g (6.78 mmol) N-Vanillylamphetamine (±)-18 at 0° 1.38 ml (7.89 mmol) S-(+)-1-Naphthyl-ethylisocyanate was dropwise added. After 1 hr. the reaction mixture was concentrated and the residue chromatographed on a silica gel column (50 mm diam., 25 cm length, 1 lbs pressure, CH₂Cl₂:MeOH=100:1 to 80:1) to give 0.76 (24%) of the less polar urea $[α]_D+72.4°$ (CHCl₃), 1.45 g (47%) mixing fraction and 0.79 g (26%) of the more polar urea as foams. Compounds 19 and 20 were 95% pure according to analytical HPLC: MS (EI) (for 19 and 20): 469 (M++1,1). Thermolysis of 19 and 20 in refluxing butanol afforded the N-vanillylamphetamines (+)18 and (−)-18, respectively.

As indicated previously, alcohols boil at above 90° C. are preferred comparative data is indicated below:

30 mg of a mixture of ureas 5 and 6 as illustrated in Example 3, were dissolved in 1 ml of an alcoholic solution of 0.23 mg sodium in 10 ml alcohol and refluxed for 1 hr. Samples of this solution were developed on TLC with CH₂Cl₂/MeOH=30:1 and made visible by exposure to iodine vapors.

The results obtained are listed in the table:

| Solvent | Reflux time | Starting material | Product |
| --- | --- | --- | --- |
| Methanol | 1 h | all | no |
| Ethanol | 1 h | almost all | little |
| Butanol | 1 h | 50% | 50% |
| 1-Pentanol | 1 h | little | almost all |
|  | 0.5 h | little | almost all |
| 1-Hexanol | 0.5 h | little | almost all |
|  | 1 h | no | all |

It seems strongly suggested that decomposition of ureas is not a hydrolysis but a thermal fragmentation forming optically active amine and isocyanate from urea. The latter is trapped by the solvent as a carbamate easily separated. This experimental design has the advantage of simple workup, easy recovery of amine and carbamate which can be recycled.

What is claimed is:

1. A method of producing optically active amines, and/or carbamates from optically active ureas comprising the steps of:
   (1) refluxing the optically active urea in alcohol solution wherein the alcohol is a $C_3$–$C_7$ alcohol; and
   (2) isolating the optically active amines and/or carbamates.

2. A process of claim 1 wherein the urea/alcohol mixture contains catalytic amounts of an alkali metal.

3. A process of claim 2 wherein the alkali metal is sodium.

4. A process of claim 1 wherein the alcohol is butanol.

5. A process of claim 1 wherein the alcohol is pentanol.

6. A process of claim 5 wherein the alcohol is n-pentanol.

7. A process of claim 1 wherein the alcohol is hexanol.

8. A process of claim 7 wherein the alcohol is n-hexanol.

9. A process of claim 1 wherein the alcohol is a $C_3$–$C_6$ alcohol.

10. A method of claim 1 wherein the optically active products are carbamates.

11. A method of claim 1 wherein the optically active products are amines.

12. A method of claim 1 wherein both optically active amines and optically active carbamates are products of the reaction.

13. A method of producing optically active isocyanates from optically active ureas comprising the steps of:
    (1) refluxing optically active urea in an alcohol solution wherein the alcohol is a $C_3$–$C_7$ alcohol;
    (2) isolating the optically active carbamates, and/or amines;
    (3) isolating the optically active amines and/or carbamates; and
    (4) converting the amines to isocyanates and/or converting carbamates to isocyanates.

14. A process of claim 13 wherein optically amines are reacted with phosgene in steps (4) to provide isocyanates.

15. A process of claim 13 wherein the optically active carbamates are reacted with trichlorosilane in the presense of triethylamine in step (4) to provide the isocyanates.

16. A process of claim 13 wherein the alcohol is a $C_3$–$C_6$ alcohol.

* * * * *